United States Patent [19]

Brier

[11] Patent Number: 5,319,807
[45] Date of Patent: Jun. 14, 1994

[54] MOISTURE-MANAGEMENT SOCK AND SHOE FOR CREATING A MOISTURE MANAGING ENVIRONMENT FOR THE FEET

[76] Inventor: Daniel L. Brier, 33 Angelfish Cay Dr., Key Largo, Fla. 33037

[21] Appl. No.: 67,469

[22] Filed: May 25, 1993

[51] Int. Cl.⁵ .............................................. A41B 11/00
[52] U.S. Cl. ..................... 2/239; 66/178 R; 66/185; 66/196; 66/201
[58] Field of Search ............... 2/239, 409; 66/178 R, 66/185, 178 A, 183, 184, 186, 187, 193, 196, 201

[56] References Cited

U.S. PATENT DOCUMENTS

| | | | |
|---|---|---|---|
| 3,250,095 | 5/1966 | Bird | 66/178 R |
| 4,341,096 | 7/1982 | Safrit et al. | 66/185 |
| 4,373,361 | 2/1983 | Thorneburg | 66/178 R |
| 4,467,626 | 8/1984 | Coble et al. | 66/178 R |
| 4,615,188 | 10/1986 | Hursh et al. | 66/178 R |
| 4,898,007 | 2/1990 | Dahlgren | 2/239 |
| 5,095,548 | 3/1992 | Chesebro, Jr. | 2/239 |

Primary Examiner—Clifford D. Crowder
Assistant Examiner—Gloria Hale
Attorney, Agent, or Firm—W. Thad Adams, III

[57] ABSTRACT

The invention relates to a moisture management sock and shoe. The sock includes a multi-layer moisture-wicking panel extending from a front ankle portion of the sock to a front toe portion of the sock. The moisture wicking panel is generally coextensive with an area of the foot covered by the tongue of a shoe. First and second single layer air circulation channels are formed in the sock, and extend along opposing sides of the moisture-wicking panel from the front ankle portion to the front toe portion of the sock. A moisture-management shoe includes a shoe tongue, a toe box area, and a moisture wicking inner liner residing adjacent the tongue and the toe box area for moving moisture from the foot and through the shoe for evaporation.

11 Claims, 5 Drawing Sheets

MOISTURE-MANAGEMENT SOCK AND SHOE FOR CREATING A MOISTURE MANAGING ENVIRONMENT FOR THE FEET

TECHNICAL FIELD AND BACKGROUND OF THE INVENTION

This invention relates to the creation of a moisture managing environment for the foot by providing a sock and shoe with moisture-management characteristics. The sock and shoe, when worn together, produce a relatively moisture-free environment for the foot by transporting a maximum amount of moisture away from the sock and shoe for eventual dissipation to the atmosphere. The invention is especially suited for athletic or sports dress, since the foot tends to perspire the most during periods of heavy activity. However, the sock and/or shoe of the present invention are likewise suited for those who naturally perspire heavily, or those who simply wish to maintain a drier environment for the foot.

Although it is preferred that the shoe and sock of the present invention be worn together for optimal wetness control, each garment can be worn separately for achieving a high degree of moisture-management. Accordingly, the moisture-management sock is designed to control the wetness of perspiration from the foot, regardless of the type shoe with which it is worn. Air circulation channels formed in the sock allow free passage of air into and out of the shoe to enhance moisture evaporation. Likewise, the moisture-management shoe is designed to remove wetness from the foot and sock, regardless of the sock with which it is worn. A moisture wicking liner in the shoe interior helps draw moisture from the sock, where it can be passed through the shoe and to the atmosphere.

By combining the features of the moisture-management sock and shoe, an environment is created which can provide significantly more effective moisture-management for the feet, beyond that created when either garment is worn separately. When the particular fabrics and components of the sock and shoe are in surface contact with each other, an integral system for moving moisture from the foot to the sock and through the shoe is developed. This overall system produces a novel "cover" for the foot which comprises a single moisture-moving composite.

In addition to the added comfort resulting from a relatively dry foot, the present invention helps retard the growth of harmful bacteria, fungus, and other related foot conditions. Athletes' foot is one such problem which can effect anyone, regardless of their exercise or recreation level. By providing a drier environment for the foot, this problem can be treated more effectively and cured much quicker.

SUMMARY OF THE INVENTION

Therefore, it is an object of the invention to provide a moisture-management sock and shoe for creating a relatively moisture-free environment for the foot.

It is another object of the invention to provide a moisture-management sock and shoe which, when worn together, maximizes wetness control and helps retard the growth of bacteria and foot fungus.

It is another object of the invention to provide a moisture-management shoe and sock which can be worn separately with non-moisture managing apparel, while still maintaining a high level of moisture-management for the foot.

It is another object of the invention to provide a moisture-management sock with a full cushion sole for providing added comfort and protection to the foot of the wearer.

It is another object of the invention to provide moisture-management sock with a full cushion sole which includes moisture wicking fibers for moving moisture away from the skin.

It is another object of the invention to provide a moisture-management sock which includes air circulation channels for allowing free air passage into and out of the shoe.

It is another object of the invention to provide a moisture-management sock which includes a moisture wicking panel for moving moisture away from the skin of the wearer.

It is another object of the invention to provide a moisture-management sock which includes a toe-box area constructed of moisture wicking fibers for moving moisture away from the toes.

It is another object of the invention to provide a moisture-management shoe including a moisture wicking liner for wicking moisture from the sock and through the shoe for evaporation.

It is another object of the invention to provide a moisture-management shoe which includes a moisture wicking liner on the inner surface of the shoe tongue for moving moisture from the top of the foot and through the shoe.

It is another object of the invention to provide a moisture-management shoe which includes a shoe tongue having a moisture wicking liner designed to cooperate with the moisture wicking panel of a moisture-management sock to more efficiently transport moisture away from the sock and through the shoe.

These and other objects of the present invention are achieved in the preferred embodiments disclosed below by providing a moisture-management sock knitted of a body yarn, and a moisture-management shoe including a inner moisture wicking liner.

According to one preferred embodiment of the invention, the sock includes a multi-layer moisture-wicking panel extending from a front ankle portion of the sock to a front toe portion of the sock. The panel includes a hydrophobic and hydrophilic yarns, and is generally co-extensive with an area of the foot covered by the tongue of a shoe. The hydrophobic wicking yarn is integrated into the knitted structure of the body yarn of the sock and resides adjacent to the skin of the wearer. The hydrophilic moisture-dispersion yarn is integrated into the knitted structure of the body yarn of the sock. This yarn resides on an outer surface of the sock, away from the skin of the wearer, to receive and disperse moisture wicked away from the skin by the hydrophobic wicking yarn. First and second single layer air circulation channels are formed in the sock, and extend along opposing sides of the moisture-wicking panel from the front ankle portion to the front toe portion of the sock. The channels are adapted to cooperate with the moisture-wicking panel and a shoe to promote air circulation between the sock and the shoe.

According to another preferred embodiment of the invention, the body yarn, hydrophobic wicking yarn, and hydrophilic yarn of the moisture wicking panel are plaited together. The wicking yarn resides adjacent to the skin of the wearer and the hydrophilic yarn resides on an outer surface of the sock away from the skin of the wearer.

Preferably, the body yarn, hydrophobic wicking yarn, and hydrophilic yarn of the moisture wicking panel are terry-knit.

Preferably, the air circulation channels are substantially flat-knit.

According to another preferred embodiment of the invention, the sock further includes a heel portion, a sole portion, and a toe portion. The heel, sole and toe portions include a hydrophobic wicking yarn integrated into the body yarn of the sock for residing in skin contact, and for transporting moisture away from the skin of the wearer.

Preferably, the hydrophobic wicking yarn of the heel, sole and toe portions and the body yarn are plaited together and terried for providing added comfort and protection to the foot of the wearer.

According to yet another preferred embodiment of the invention, the toe portion further includes a hydrophilic yarn plaited together with the hydrophobic wicking yarn and the body yarn. The hydrophilic yarn resides on an outer surface of the toe portion away from the skin for receiving and dispersing moisture wicked outwardly by the hydrophobic wicking yarn.

According to yet another preferred embodiment of the invention, the sock further includes an elastic yarn integrated into the body yarn for radially extending about the arch area of the foot of the wearer, and for providing a secure fit to hold the moisture wicking panel in a relatively stationary position atop the foot of the wearer.

According to yet another preferred embodiment of the invention, the sock further includes an over-toe panel for residing substantially above the toes of the wearer, and adjacent to one end of the wicking panel. The over-toe panel includes a hydrophobic wicking yarn integrated into the body yarn of the sock for residing in skin contact and for wicking moisture away from the skin of the wearer.

Preferably, the over-toe panel further includes a hydrophilic yarn plaited together with the hydrophobic wicking yarn and the body yarn. The hydrophilic yarn resides on an outer surface of the over-toe panel away from the skin for receiving and dispersing moisture wicked outwardly by the hydrophobic wicking yarn.

According to another preferred embodiment of the invention, the sock further includes a top calf portion including elastic yarns integrated into the body yarn for holding the sock up on the leg of the wearer.

A moisture-management shoe includes a shoe tongue, a toe box area, and a moisture wicking inner liner residing adjacent the tongue and the toe box area for moving moisture from the foot and through the shoe for evaporation. The moisture wicking liner includes first and second fabric layers. The first fabric layer is constructed of hydrophobic wicking yarn for residing next to the foot of the wearer, and for wicking moisture outwardly away from the foot of the wearer. The second fabric layer is constructed of hydrophilic yarn residing adjacent the first fabric layer for receiving and dispersing moisture wicked outwardly from the first fabric layer. A conventional sew stitch attaches the moisture wicking liner to an interior surface of the shoe tongue and the toe box area.

According to one preferred embodiment of the invention, the first fabric layer is constructed of an integrally knit fabric having hydrophobic yarn on an inner fabric face thereof for residing in foot contact, and having hydrophilic yarn on an outer fabric face in surface contact with the second fabric layer.

According to another preferred embodiment of the invention, the second fabric layer is constructed of a knit fabric having an inner fabric face residing in surface contact with the first fabric layer. The inner fabric face has a brushed finish to enhance the ability of the second fabric layer to receive and disperse moisture wicked outwardly from the first fabric layer.

According to yet another preferred embodiment of the invention, the shoe tongue includes a foam padding layer and an exterior fabric layer. The foam padding layer resides adjacent to and in surface contact with the second fabric layer of the moisture wicking liner. The exterior fabric layer resides in surface contact with the foam padding layer and comprises the outermost layer of the shoe tongue.

Preferably, the attachment means includes sewing the inner liner to the interior surface of the tongue and the toe box area.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Moisture-management Sock

Figure 1:
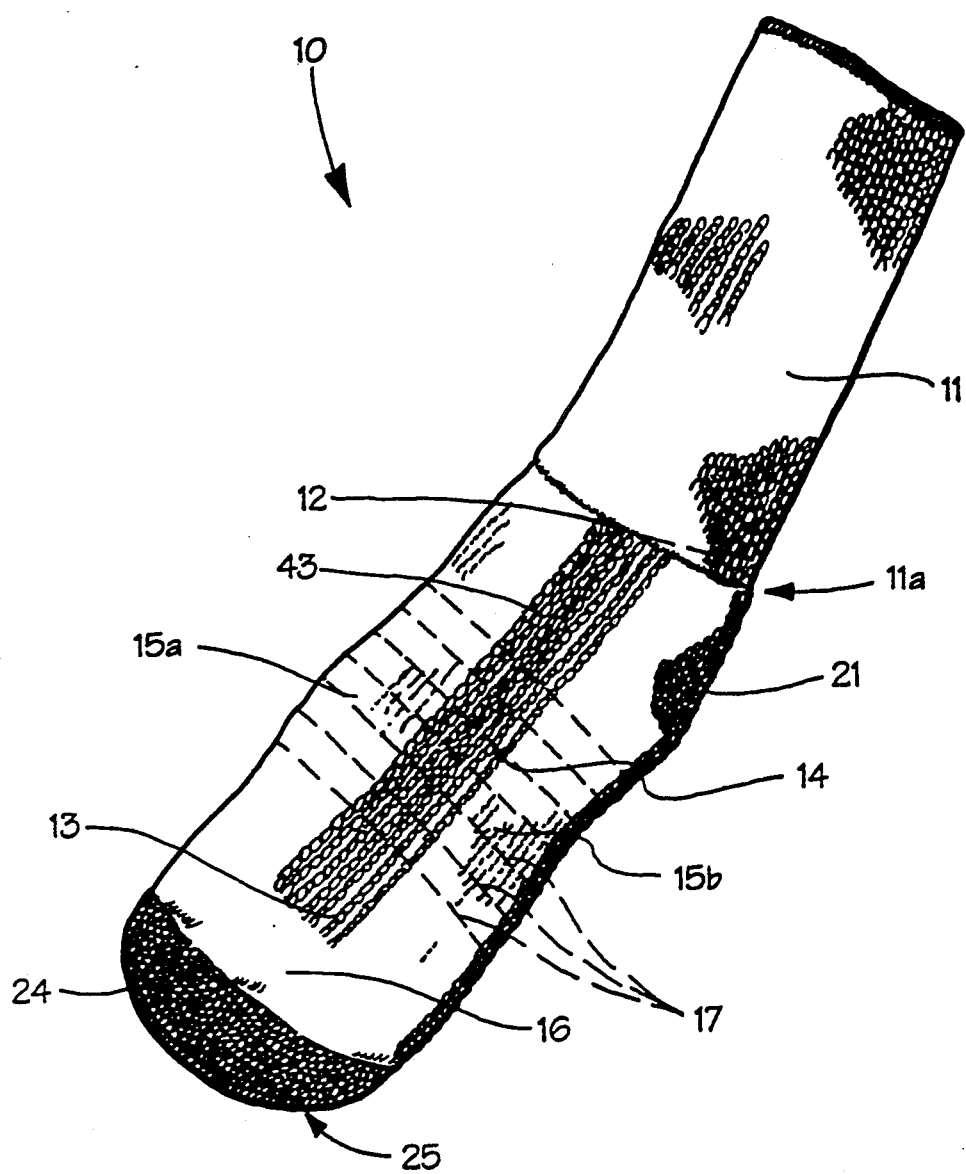
FIG. 1 is a front perspective view of a moisture-management sock according to a preferred embodiment of the invention.

Referring now specifically to the drawings, a moisture-management sock according to the present invention is illustrated in FIG. 1 and shown generally at reference numeral 10. The sock 10 is particularly suited for wear with a moisture-management shoe 50, illustrated in FIG. 4, for creating a complete moisture managing environment for the feet. However, it is noted that the sock 10 or shoe 50 may be worn separately with non-moisture managing apparel, while still maintaining a drier environment for the feet.

FIG. 1 illustrates a front view of the sock 10. As shown, the sock 10 preferably includes a leg portion 11 extending from the ankle area 11a upwardly toward the calf area of the wearer. According to another embodiment (not shown), sock 10 does not include a leg portion 11, and is suitable as, for example, a low-cut golf or tennis sock. Leg portion 11 is preferably constructed of nylon and acrylic yarns, and elastic yarns such as spandex for supporting the sock 10 on the leg. The yarns of the leg portion 11 may be knitted as shown in FIG. 1, with a rib stitch to provide a ribbed effect. According to another embodiment, the leg area 11 is flat knit. Other yarns conventionally used in the manufacture of socks, such as cotton, may be substituted in the leg area 11 for achieving similar feel and support.

A moisture wicking panel 14 extends generally from the base of the leg portion 11, at a front ankle portion 12, to a front toe portion 13. Preferably, the moisture wicking panel 14 is positioned to reside directly beneath and in surface contact with the tongue of a shoe. Accordingly, the moisture wicking panel 14 acts to draw moisture from the foot and to the area beneath the shoe tongue where the moisture can be more readily dispersed and evaporated.

According to one embodiment, the underlying body yarns of the wicking panel 14 include acrylic and nylon. However, other conventional body yarns such as cotton may be substituted as desired. Preferably, the wicking panel 14 is created by "chopping in" two moisture-management yarns; one end of a hydrophobic wicking yarn 41 and one end of a hydrophilic yarn 43. For example, the "Coolmax" and "Hydrofil" yarns manufactured by DuPont may be used, respectively, for the hydrophobic and hydrophilic yarns 41 and 43 of the wicking panel 14.

Figure 2:
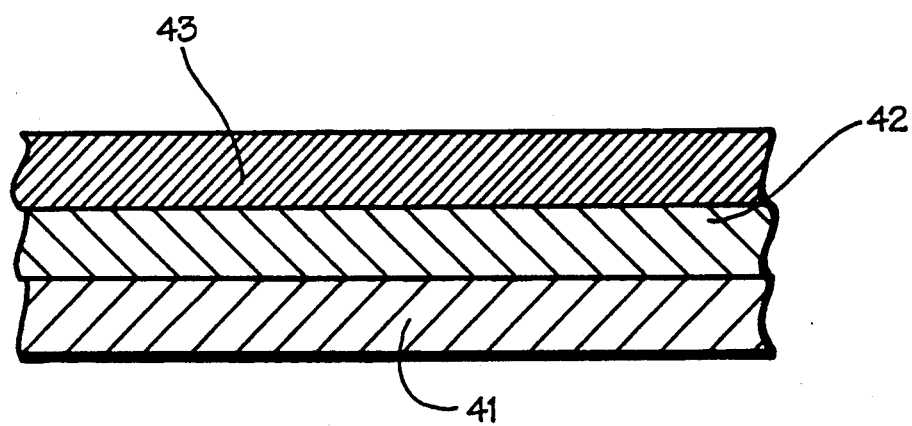
FIG. 2 is a partial schematic cross-section of the moisture-management sock, illustrating in exaggerated detail the fabric construction of the moisture wicking panel.

The hydrophobic wicking yarn 41, body yarn 42, and hydrophilic yarn 43 are plaited together and terried in moisture wicking panel 14. FIG. 2 shows an exaggerated cross-sectional view of the preferred fabric construction in this area. Preferably, the wicking yarn 41 and body yarn 42 are plaited to the inside surface of the wicking panel 14, closest to the skin of the foot. Both yarns function to wick and transport moisture away from the foot. The hydrophilic yarn 43 is preferably plaited to the outside, where it acts to pull and disperse moisture wicked outwardly from the hydrophobic wicking yarn 41 and body yarn 42. According to one embodiment, the hydrophilic yarn 43 forms the outer surface of the wicking panel 14 in the sock 10.

Referring again to FIG. 1, first and second air circulation channels 15a and 15b are formed in the sock 10, extend along opposing sides of the moisture wicking panel 14. The channels 15a, 15b are adapted to cooperate with the moisture wicking panel 14 and a shoe to promote air circulation between the sock 10 and the shoe. Preferably, a third channel comprising an over-toe panel 16 is formed adjacent to and extending along one end of the moisture wicking panel 14 at an area substantially above the toes of the wearer.

Preferably, the yarns of channels 15a, 15b, and over-toe panel 16 are flat knit, instead of terry knit like the moisture wicking panel 14. The contrast in thickness resulting from the flat knit and terry knit areas provides a sufficient space for air circulation between the foot and shoe. As best shown in FIG. 1, the channels 15a, 15b, and over-toe panel 16 cooperate to form a U-shaped air passage for allowing air flow into and out of the shoe. This feature also encourages air movement between the toes to enhance moisture transport and evaporation as each step is taken by the wearer. Moreover, the continuous circulation of air about the moisture wicking panel 14 acts to further enhance evaporation of moisture wicked into this area.

Preferably, the first and second channels 15a and 15b include the acrylic and nylon body yarns of leg portion 11. However, unlike the leg portion 11 as described above, channels 15a and 15b do not include a complete area of elastic yarns or spandex. Instead, the elastic yarns 17 are introduced only in the arch or instep area of the foot. According to a preferred embodiment, the elastic yarns 17 extend radially over the top area of the foot, and act to maintain the moisture wicking panel 14 in a relatively stationary position atop the foot of the wearer and below the tongue of the shoe.

Figure 3:
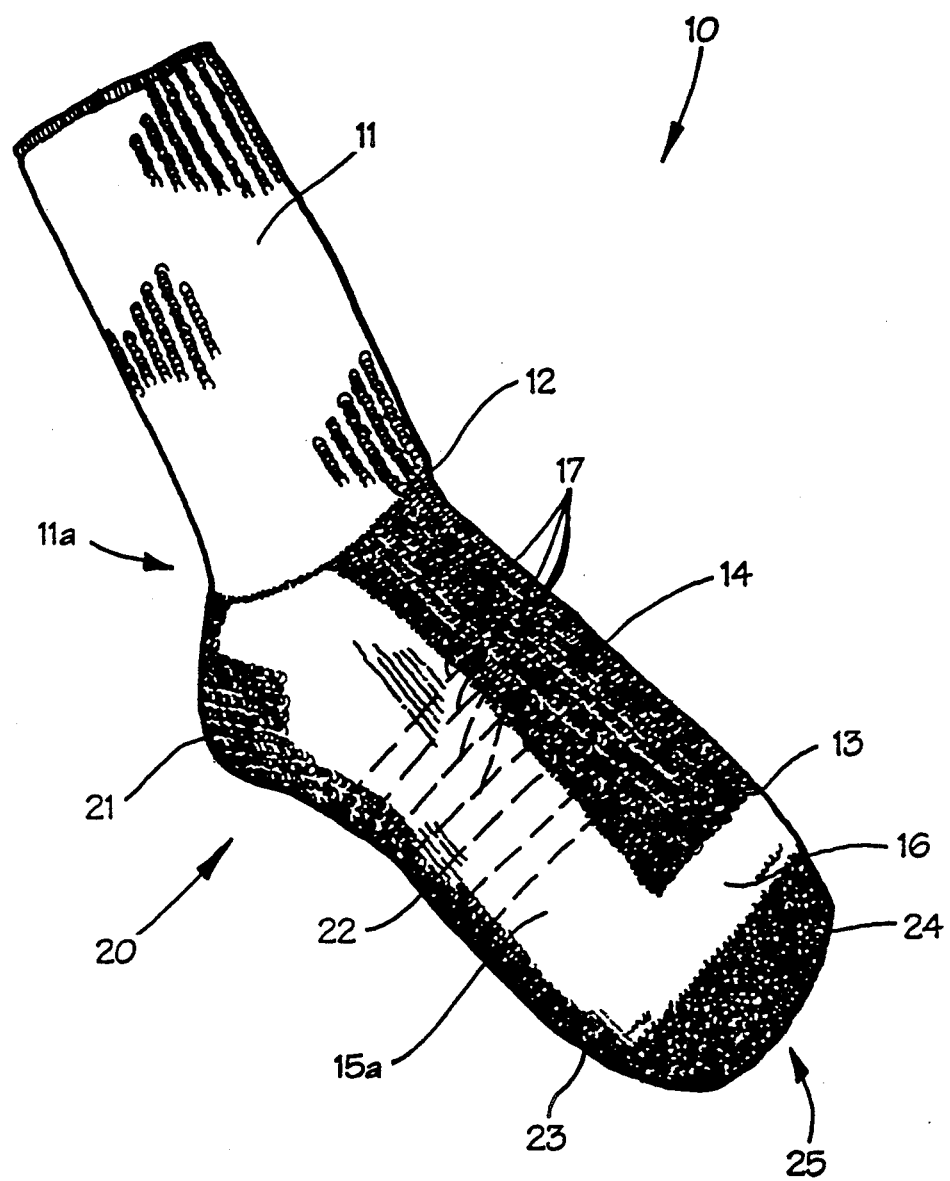
FIG. 3 is a side elevation of the sock illustrated in FIG. 1.

In FIG. 3, a full cushion sole 20 of sock 10 is illustrated. As shown, the full cushion sole 20 includes a heel portion 21, body portion 22, under-toe portion 23, and toe-box portion 24. The cushioned effect in this area is provided by terry loops which help soften the impact and pounding received by the foot, particularly during periods of recreation and exercise.

In addition to the body yarns, the full cushion sole 20 of sock 10 includes hydrophobic wicking yarns such as polyester or polypropylene. The wicking yarn and the body yarn are knitted together into common terry loops with the wicking yarn plaited to the inside, closest to the skin of the wearer. Again, the body yarns are preferably acrylic and nylon, but other yarns would be suitable.

The toe area 25 of sock 10 includes the under-toe portion 23, toe-box portion 24, and over-toe panel 16. In addition to the hydrophobic wicking yarns and body yarn of the under-toe 23 and toe-box 24 portions of the full cushion sole 20, the toe area 25 further includes hydrophilic yarns for pulling and dispersing moisture wicked outwardly by the hydrophobic yarns. Preferably, the under-toe 23 and toe-box 24 portions are terry knit with the hydrophobic yarns plaited closest to the skin, and the hydrophilic yarns plaited to the outer surface. As noted above, the over-toe panel 16 forms a third air circulation channel, and is preferably flat knit. In the over-toe panel 16, hydrophobic yarns reside closest to the skin with the hydrophilic yarns residing on the outer surface of the sock 10.

The plaited construction of hydrophobic and hydrophilic yarns creates a "push-pull" effect, wherein body heat "pushes" moisture along the fibers of the wicking yarn away from the skin and into the "pull" of the hydrophilic outer yarns. Once transported and dispersed in the outer yarns, the moisture can more readily evaporate with the aid of air circulation channels 15a and 15b, and over-toe panel 16.

The selection of fibers, yarns, and fabric structure, be it a knit or woven structure, can have a material effect on the movement of moisture. In one embodiment, modacrylics can be substituted for the acrylic yarns described above without materially effecting the comfort of the sock. Additionally, the wicking yarns, such as nylon, polyester, and polypropylene, can be textured to enhance the degree of moisture movement in the fibers.

Moisture-management Shoe

Figure 4:
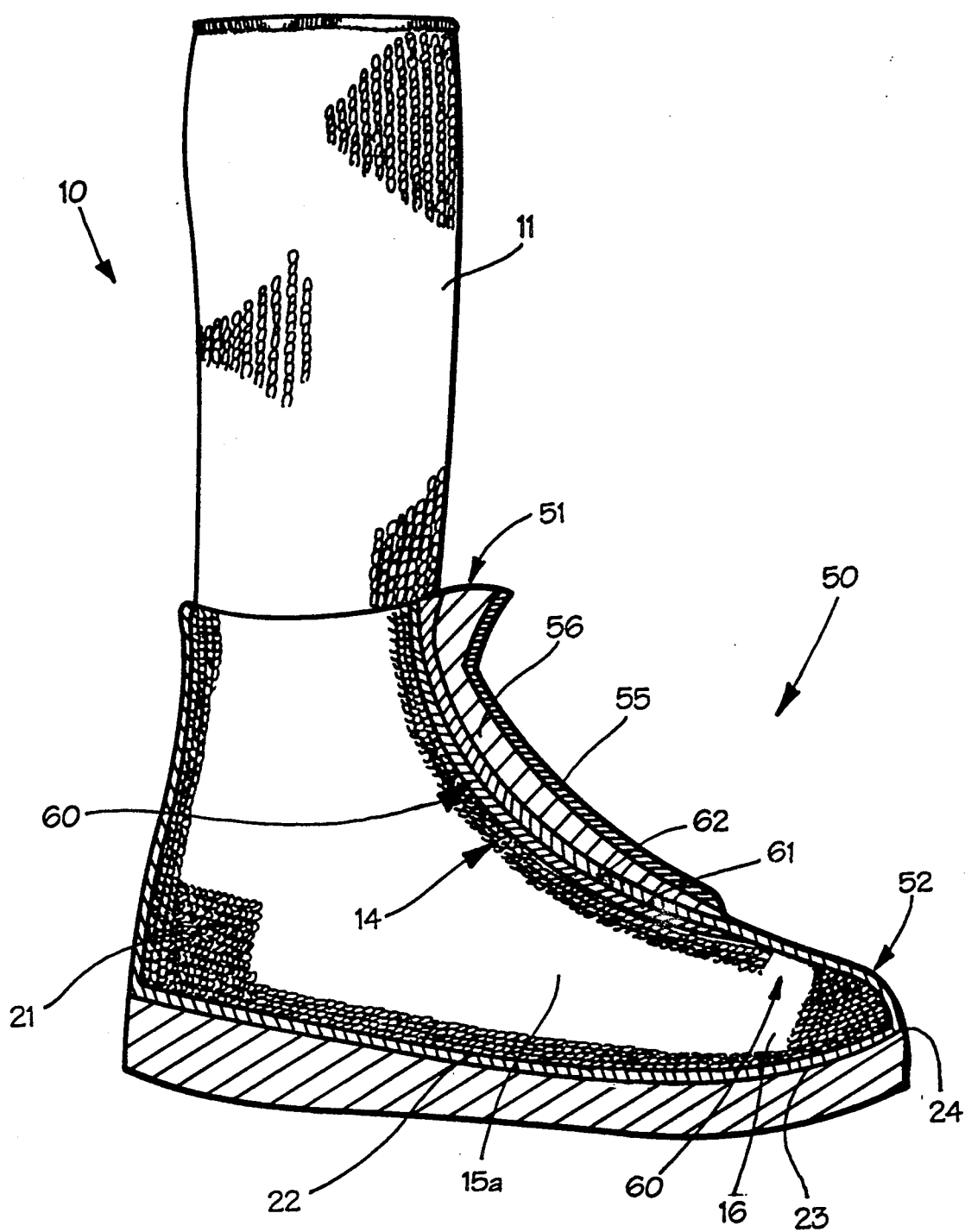
FIG. 4 is a side elevation of a moisture-management shoe worn together with the sock of FIGS. 1 and 3.

A moisture-management shoe according to the present invention is illustrated in FIG. 4 and shown generally at reference numeral 50. As noted earlier, the moisture-management shoe 50 is particularly suited for wear with the moisture-management sock 10 described above. The sock 10 and shoe 50 create a complete and effective moisture managing environment for the feet.

FIG. 4 represents a cross-sectional side view of the shoe 50 worn together with moisture-management sock 10. The shoe 50 includes a moisture wicking liner 60 attached to the inner surface of the shoe tongue 51 and toe box area 52. The moisture wicking liner 60 may be suitably attached by any conventional sewing means, or may be integrally formed to the inner surface fabric of the shoe 50.

Figure 5:
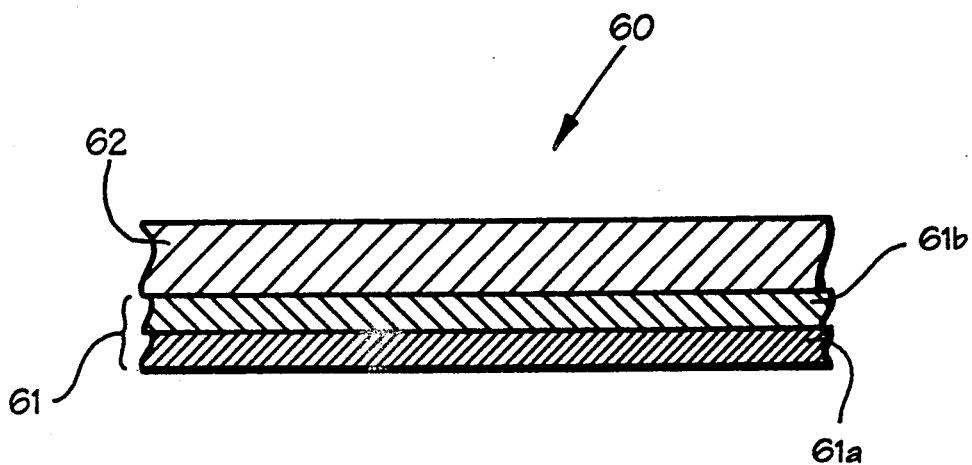
FIG. 5 is a fragmentary cross-sectional view of the moisture wicking liner according to one preferred embodiment of the moisture-management shoe.

FIG. 5 is a sectional view of the moisture wicking liner 60 showing first and second fabric layers 61 and 62. The first fabric layer 61 is constructed of hydrophobic wicking yarns for residing next to the foot of the wearer, closest to the source of perspiration or moisture. This layer is designed particularly to wick moisture outwardly, away from the foot of the wearer.

According to one preferred embodiment, the first fabric layer 61 comprises an integrally knit hi-component fabric having hydrophobic wicking yarns on an inner fabric face 61a for residing in contact with the foot or sock of the wearer, and an outer fabric face 61b residing in surface contact with the second fabric layer 62. The outer fabric face 61b of the first fabric layer 61 is formed of hydrophilic yarns for receiving and dispersing moisture wicked outwardly by the inner fabric face. Thus, the fabric creates a "push-pull" effect, wherein body heat "pushes" moisture along the inner fibers of the wicking yarn away from the foot, and into the "pull" of the outer hydrophilic yarns. Preferably, the wicking yarns of the inner fabric face 61a are polyester or polypropylene, and the hydrophilic yarns of the outer fabric face are hydrophilic nylon or cotton.

The second fabric layer 62 resides in surface contact with the outer face 61b of the first fabric layer 61, and is preferably constructed of hydrophilic fibers. These fibers act to further pull and disperse moisture wicked outwardly by the first fabric layer 61. Preferably, the surface of the second fabric layer 62 residing adjacent to the first fabric layer 61 is brushed or sanded to enhance its ability to receive moisture from the outer face 61b of the first fabric layer 61. The hydrophilic fibers of the second fabric layer 62 are preferably chosen from the fiber group consisting of hydrophilic nylon or cotton.

In one embodiment, the moisture wicking liner extends from the uppermost interior portion of the shoe tongue 51 to an area of the toe box 52 just beneath the toes of the wearer. According to another embodiment (not shown), the moisture wicking liner 60 substantially encompasses the entire surface area of the shoe interior.

Figure 6:
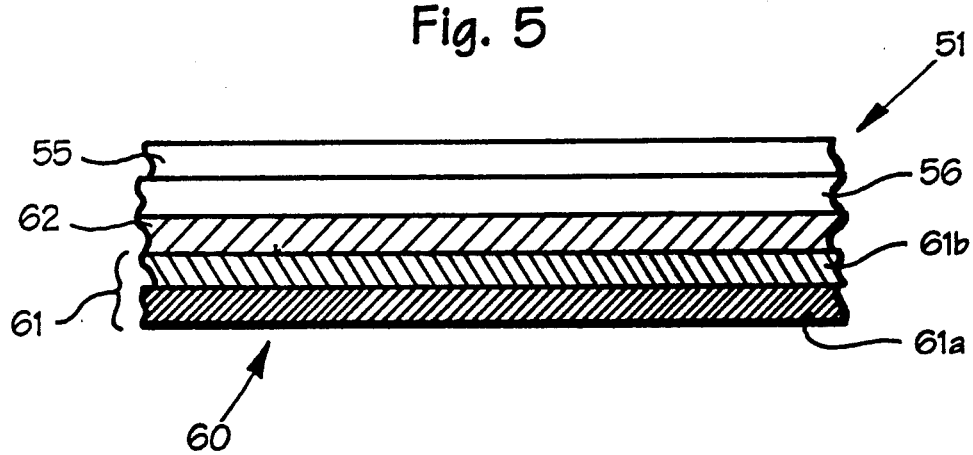
FIG. 6 is a fragmentary cross-sectional view of the tongue of the moisture-management shoe illustrated in FIG. 4.
Figure 7:
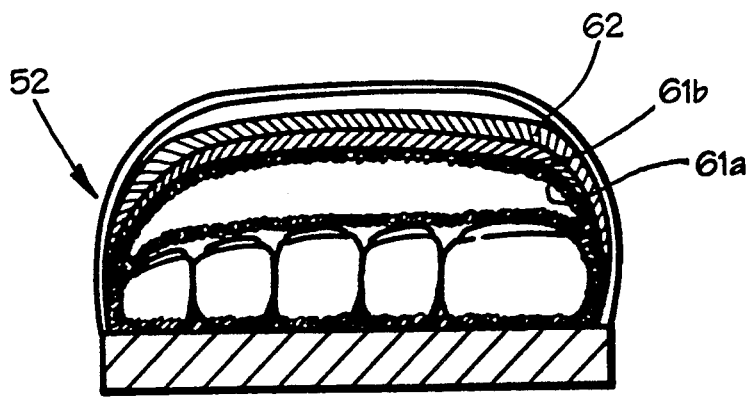
FIG. 7 is a cross-sectional view of the toe-box area of the shoe illustrated in FIG. 4.

Cross-sectional views of the tongue 51 and toe box 52 are shown, respectively, in FIGS. 6 and 7. The tongue 51 includes an exterior layer 55, such as nylon, and a foam padding layer 56. According to one preferred embodiment, the moisture wicking liner 60 is attached to the under surface of the foam padding layer 56 by a conventional sewing technique. According to another embodiment, the moisture wicking liner 60 is integrally formed to the under surface of the foam padding layer 56.

The moisture wicking liner 60 is included in the toe box 52 for further wicking and transporting moisture from the toes of the wearer to the tongue 51 of the shoe 50. Preferably, the first and second layers 61 and 62 of the moisture wicking liner 60 are in exact registration from the shoe tongue 51 to the toe box 52. According to one embodiment, the wicking liner 60 is continuous from the shoe tongue 51 to the toe box 52. Alternately, the wicking liner 60 may be sewn separately in the toe box 52, or may be integrally formed to the inner surface of the toe box 52.

Once moisture has been moved outwardly and upwardly by the moisture wicking liner 60 of the shoe tongue 51 and toe box 52, it is then drawn through the foam padding 56 and nylon exterior 55 layers of the shoe tongue 51 where it thereafter evaporates. Thus, when used together with sock 10, wetness can be more effectively and efficiently removed from the foot, since the sock 10 is particularly designed to transport moisture away from the foot and to the moisture wicking panel 14 residing beneath the tongue 51 of the shoe 50. From the moisture wicking panel 14 of sock 10, moisture is further transported through the moisture wicking liner 60 and shoe tongue 51 for eventual evaporation.

A moisture-management sock and shoe according to the present invention are described above. Various details of the invention may be changed without departing from its scope. Furthermore, the foregoing description of the preferred embodiment of the invention is provided for the purpose of illustration only and not for the purpose of limitation—the invention being defined by the claims.

I claim:

1. A moisture-management sock knitted of a body yarn, comprising:
    (a) a relatively thick multi-layer moisture-wicking panel extending from a front ankle portion of the sock to a front toe portion of the sock generally co-extensive with an area of the foot covered by the tongue of a shoe, said moisture-wicking panel including:
    (i) a hydrophobic wicking yarn integrated into the knitted structure of the body yarn of the sock to substantially reside adjacent to the skin of the wearer; and
    (ii) a hydrophilic moisture-dispersion yarn integrated into the knitted structure of the body yarn of the sock to substantially reside on an outer surface of the sock away from the skin of the wearer to receive and disperse moisture wicked away from the skin by the hydrophobic wicking yarns;
    (b) first and second single fabric layers defining first and second air circulation channels formed in the sock and extending along opposing sides of said moisture-wicking panel from the front ankle portion to the front portion of the sock, said single fabric layers being thinner than said thick panel; and
    (c) an over-toe panel comprising a relatively thin single fabric layer defining a third air circulation channel for residing substantially above the toes of the wearer, and adjacent to one end of said moisture wicking panel; said over-toe panel including a hydrophobic wicking yarn integrated into the body yarn of said sock for substantially residing in skin contact and for wicking moisture away from the skin of the wearer; whereby said first, second and third air circulation channels cooperate with each other and said thick panel to form a U-shaped air passage extending adjacent to the opposing sides and end of said relatively thick, moisture wicking panel to promote air circulation between the sock and the shoe.

2. A moisture-management sock according to claim 1, wherein said body yarn, hydrophobic wicking yarn, and hydrophilic yarn of the moisture wicking panel are plaited together; said wicking yarn residing substantially adjacent to the skin of the wearer and said hydrophilic yarn residing substantially on an outer surface of the sock away from the skin of the wearer.

3. A moisture-management sock according to claim 2, wherein said body yarn, hydrophobic wicking yarn, and hydrophilic yarn of said moisture wicking panel are terry-knit.

4. A moisture-management sock according to claim 1, wherein said air circulation channels are substantially flat-knit.

5. A moisture-management sock according to claim 1, further comprising a heel portion, a sole portion, and a toe portion; said heel, sole and toe portions including a hydrophobic wicking yarn integrated into the body yarn of said sock for substantially residing in skin contact, and for transporting moisture away from the skin of the wearer.

6. A moisture-management sock according to claim 5, wherein the hydrophobic wicking yarn of said heel, sole and toe portions and said body yarn are plaited together and terried for providing added comfort and protection to the foot of the wearer.

7. A moisture-management sock according to claim 5, wherein said toe portion further includes a hydrophilic yarn plaited together with said hydrophobic wicking yarn and said body yarn, said hydrophilic yarn substantially residing on an outer surface of said toe portion away from the skin for receiving and dispersing moisture wicked outwardly by said hydrophobic wicking yarn.

8. A moisture-management sock according to claim 1, further comprising an elastic yarn integrated into said body yarn for radially extending about the arch area of the foot of the wearer, and for providing a secure fit to hold said moisture wicking panel in a relatively stationary position atop the foot of the wearer.

9. A moisture-management sock according to claim 1, further comprising an over-toe panel for residing substantially above the toes of the wearer, and adjacent to one end of said wicking panel; said over-toe panel including a hydrophobic wicking yarn integrated into the body yarn of said sock for substantially residing in skin contact and for wicking moisture away from the skin of the wearer.

10. A moisture-management sock according to claim 9, wherein said over-toe panel further includes a hydrophilic yarn plaited together with said hydrophobic wicking yarn and said body yarn, said hydrophilic yarn substantially residing on an outer surface of said over-toe panel away from the skin for receiving and dispersing moisture wicked outwardly by said hydrophobic wicking yarn.

11. A moisture-management sock according to claim 1, further comprising a top calf portion including elastic yarns integrated into said body yarn for holding the sock up on the leg of the wearer.

* * * * *